United States Patent
Wey et al.

(10) Patent No.: US 8,466,521 B2
(45) Date of Patent: Jun. 18, 2013

(54) HYDROGEN ION-SENSITIVE FIELD EFFECT TRANSISTOR AND MANUFACTURING METHOD THEREOF

(75) Inventors: Chin-Long Wey, Hsinchu (TW); Chin-Fong Chiu, Hsinchu (TW); Ying-Zong Juang, Hsinchu (TW); Hann-Huei Tsai, Hsinchu (TW); Chen-Fu Lin, Hsinchu (TW)

(73) Assignee: National Chip Implementation Center National Applied Research Laboratories, Hsinchu (TW)

( * ) Notice: Subject to any disclaimer, the term of this patent is extended or adjusted under 35 U.S.C. 154(b) by 580 days.

(21) Appl. No.: 12/724,435

(22) Filed: Mar. 16, 2010

(65) Prior Publication Data
US 2011/0169056 A1 Jul. 14, 2011

(30) Foreign Application Priority Data
Jan. 11, 2010 (TW) .............................. 099100444 A

(51) Int. Cl.
*H01L 31/119* (2006.01)
(52) U.S. Cl.
USPC ............ 257/414; 257/48; 257/226; 257/288; 257/350

(58) Field of Classification Search
USPC .......................... 257/48, 288, 350, 414, 226
See application file for complete search history.

(56) References Cited

U.S. PATENT DOCUMENTS
7,321,143 B2 * 1/2008 Kunath et al. ................. 257/288

\* cited by examiner

*Primary Examiner* — Samuel Gebremariam
(74) *Attorney, Agent, or Firm* — Stites & Harbison PLLC; Juan Carlos A. Marquez, Esq.

(57) ABSTRACT

A hydrogen ion-sensitive field effect transistor and a manufacturing method thereof are provided. The hydrogen ion-sensitive field effect transistor includes a semiconductor substrate, an insulating layer, a transistor gate, and a sensing film. A gate area is defined on the semiconductor substrate having a source area and a drain area. The insulating layer is formed within the gate area on the semiconductor substrate. The transistor gate is deposited within the gate area and includes a first gate layer. Further, the first gate layer is an aluminum layer, and a sensing window is defined thereon. The sensing film is an alumina film formed within the sensing window by oxidizing the first gate layer. Thus, the sensing film is formed without any film deposition process, and consequently the manufacturing method is simplified.

5 Claims, 5 Drawing Sheets

HYDROGEN ION-SENSITIVE FIELD EFFECT TRANSISTOR AND MANUFACTURING METHOD THEREOF

BACKGROUND OF THE INVENTION

1. Technical Field

The present invention relates to a hydrogen ion-sensitive field effect transistor (FET) and a manufacturing method thereof. More particularly, the present invention relates to a hydrogen ion-sensitive FET applicable to a biosensor for measuring pH values and compatible with a transistor manufacturing process, and a method for manufacturing the hydrogen ion-sensitive FET.

2. Description of Related Art

As an analyzing device for measuring trace components, the so-called biosensor transforms information regarding the various measurement targets (e.g., glucose, blood sugar concentration, potassium ion concentration, cholesterol, etc.) in biomaterials into electronic or optical signals by use of bio-sensing elements (e.g., enzymes, antibodies, etc.) and physical principles so that subsequent analysis and processing are made easier.

However, during the measuring process, variations in pH values tend to affect the degree of ionization of various chemical substances in the biomaterials and alter the biomaterials or the measurement targets' activities. Therefore, a biosensor capable of measuring pH values is needed in order to provide accurate measurement of other bio-information items.

FIG. 1 is a schematic cross-sectional view of an ion-sensitive FET in the prior art.

Currently, biosensors commonly used for measuring pH values are ion-sensitive FETs (ISFETs), which are electrochemical sensing devices proposed by Piet Bergveld in 1970. ISFETs are advantageous in that they are miniaturized and suitable for automated measurement.

Referring to FIG. 1, the ISFET is similar in structure to a complementary metal oxide semiconductor (CMOS) manufactured by an integrated circuit (IC) manufacturing process. The ISFET includes a semiconductor substrate 10, a drain area 11, a source area 12, an insulating layer 13, an ion sensing film 14, a metallic layer 15, epoxy resin 16, an external reference electrode 17, and a buffer solution 20.

The ISFET differs from a CMOS in that a metallic gate of the CMOS is replaced by the ion sensing film 14, the buffer solution 20, and the external reference electrode 17. The ISFET can be immersed in buffer solutions 20 of different pH values. When the ISFET makes contact with the buffer solutions 20, different variations in the electrical potential arise at the interface between the metallic gate (i.e., the ion sensing film 14) and the buffer solution 20, thereby changing the current. By virtue of this property and through subsequent conversion and processing of the electrical signal measured by the reference electrode 17, the pH values or the concentrations of other ions in the buffer solution 20 can be evaluated.

In the last thirty years, a lot of research related to ISFETs have been conducted worldwide, as seen in research conducted on reference electrodes and miniaturization thereof, studies on ion-sensitive field effect devices using fixed enzymes, and discussion on differential front-end detection circuitries. Furthermore, attempts have also been made to look for more suitable and more stable ion sensing films, such as those made of $Si_3N_4$, $Al_2O_3$, $Ta_2O_5$, $SnO_2$, a-$WO_3$, a-Si:H, AlN, $PbTiO_3$, or the like. However, such research is still within the basic framework of the prior art described above.

BRIEF SUMMARY OF THE INVENTION

It is an objective of the present invention to provide a hydrogen ion-sensitive FET for use in a biosensor as well as a method for manufacturing the hydrogen ion-sensitive FET. By using a conductor made of AlCu alloy that is commonly found in CMOS manufacturing processes and under appropriate temperature and humidity control, a relatively compact and very thin alumina layer can be produced without any additional film deposition process. The alumina layer can be used as an ion sensing layer to measure pH values, thereby achieving the objective of measuring hydrogen ions.

It is another objective of the present invention to provide a hydrogen ion-sensitive FET and a manufacturing method thereof which can be integrated with a CMOS manufacturing process so as to reduce manufacturing costs and satisfy the demands for single chips.

To achieve the aforesaid objectives, the present invention provides a hydrogen ion-sensitive FET including: a semiconductor substrate which has a gate area defined thereon and further has a source area and a drain area; an insulating layer formed within the gate area on the semiconductor substrate; a transistor gate deposited within the gate area and having a first gate layer, wherein the first gate layer is an aluminum layer and has a sensing window defined thereon; and a sensing film formed within the sensing window, wherein the sensing film is an alumina layer formed by oxidizing the first gate layer.

To achieve the aforesaid objectives, the present invention also provides a method for manufacturing a hydrogen ion-sensitive FET which includes the steps of: providing a semiconductor substrate having a source area, a drain area, and an insulating layer formed thereon, wherein the insulating layer is provided within a gate area on the semiconductor substrate; performing a gate manufacturing process in which an aluminum layer is deposited within the gate area to form a first gate layer; defining a sensing window on the first gate layer; and forming a sensing film by exposing the sensing window of the first gate layer to an oxygen-containing gas, so as to form an alumina layer for use as the sensing film.

Implementation of the present invention at least involves the following inventive steps:

1. A hydrogen ion-sensitive FET capable of measuring pH values can be manufactured by a general CMOS manufacturing process.

2. Without additional film deposition processing, a relatively compact and very thin alumina layer can be produced and used as an ion sensing layer. Thus, the purpose of measuring hydrogen ions can be accomplished without incurring any additional manufacturing costs.

Hereinafter, the features and advantages of the present invention will be described in detail so that anyone skilled in the art can appreciate the technical disclosure of the present invention and practice the present invention accordingly, and so that the objectives and advantages of the present invention can be readily understood by anyone skilled in the art upon reviewing the disclosure, claims, and attached drawings of the present invention.

BRIEF DESCRIPTION OF THE SEVERAL VIEWS OF THE DRAWINGS

The invention as well as a preferred mode of use and advantages thereof will be best understood by referring to the following detailed description of illustrative embodiments in conjunction with the accompanying drawings, wherein.

DETAILED DESCRIPTION OF THE INVENTION

Figure 2A:
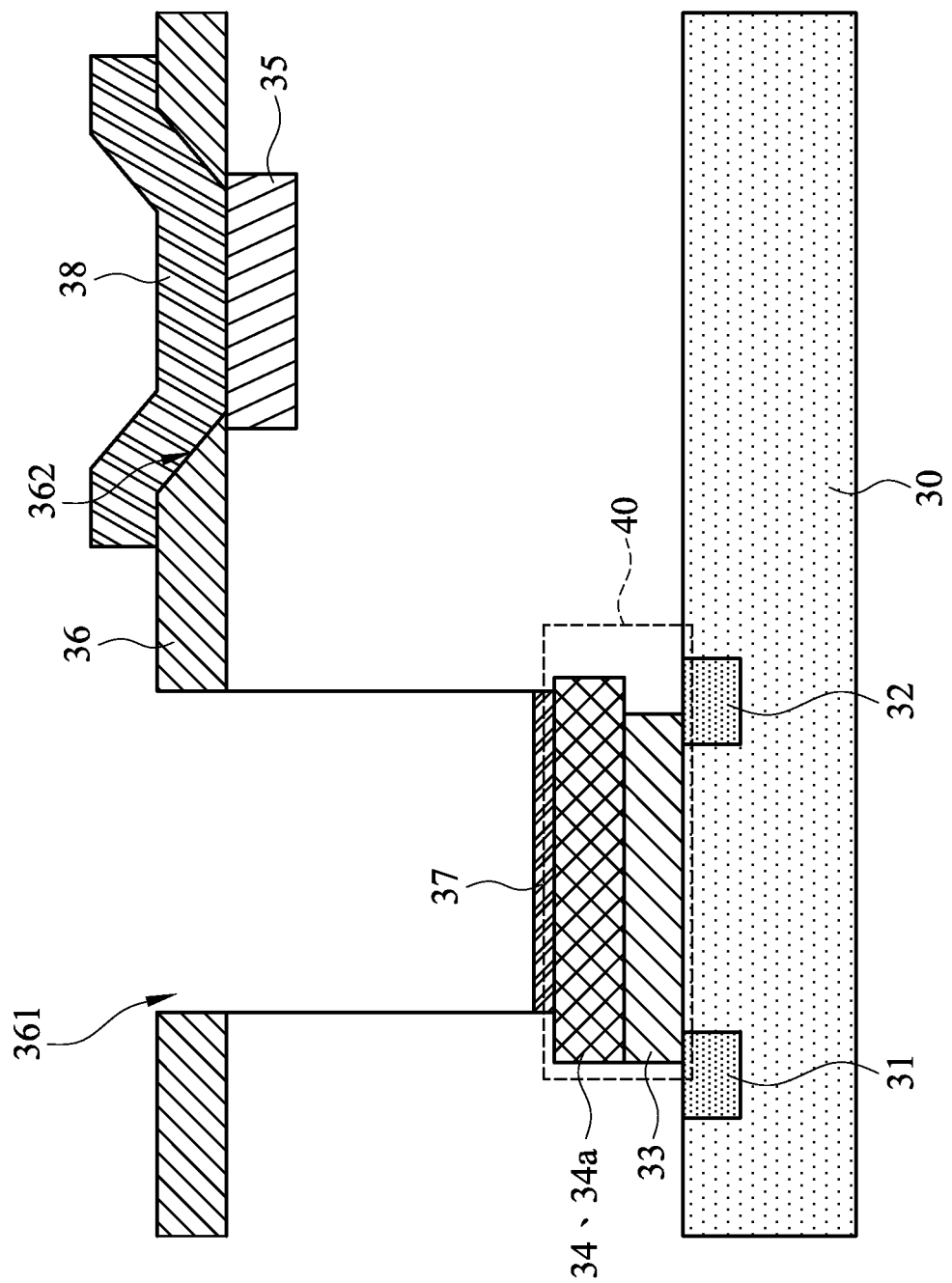
FIGS. 2A and 2B are schematic cross-sectional views of hydrogen ion-sensitive FETs according to different embodiments of the present invention respectively.

Please refer to FIG. 2A for a hydrogen ion-sensitive FET according to a first embodiment of the present invention. The hydrogen ion-sensitive FET is similar in basic structure to a CMOS and includes a semiconductor substrate 30, an insulating layer 33, a transistor gate 34, and a sensing film 37.

The semiconductor substrate 30 has a gate area 40 defined thereon and further has a drain area 31 and a source area 32. Within the gate area 40 are formed the insulating layer 33 and a first gate layer 34a, wherein the first gate layer 34a serves as the transistor gate 34. In addition, a passivation layer 36 is formed and goes through anisotropic etching in a post-process to form a first opening 361 which is etched to the first gate layer 34a. Thus, a sensing window is defined on the first gate layer 34a, and the first gate layer 34a is exposed through the sensing window.

Moreover, as the first gate layer 34a is an aluminum layer, the aluminum layer exposed through the sensing window (i.e., the first gate layer 34a within the first opening 361) will automatically oxidize under appropriate temperature control and humidity control. Thus, the oxidized aluminum layer forms a relatively compact and very thin alumina layer. As the thickness of the alumina layer will not vary greatly with time, the alumina layer can be used as the sensing film 37 which is selective to hydrogen ions.

Figure 1:
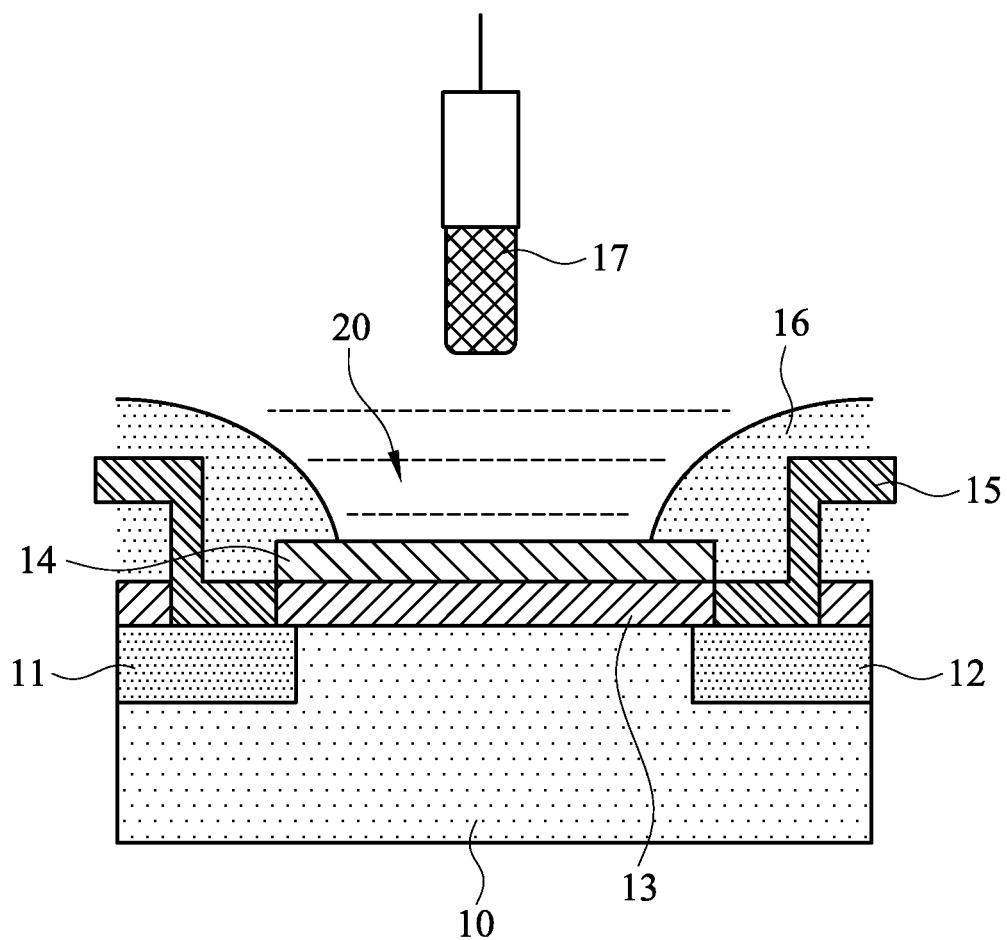
FIG. 1 is a schematic cross-sectional view of an ion-sensitive FET of the prior art.

In one embodiment, a reference electrode is externally provided and suspended in a buffer solution as in the prior art (as shown in FIG. 1). Alternatively, the reference electrode may also be fabricated into the hydrogen ion-sensitive FET. For example, as shown in the right section of FIG. 2A, a conductor 35 is formed, and the passivation layer 36 further has a second opening 362 such that a reference electrode layer 38 is disposed on the conductor 35 and exposed through the passivation layer 36.

Figure 2B:
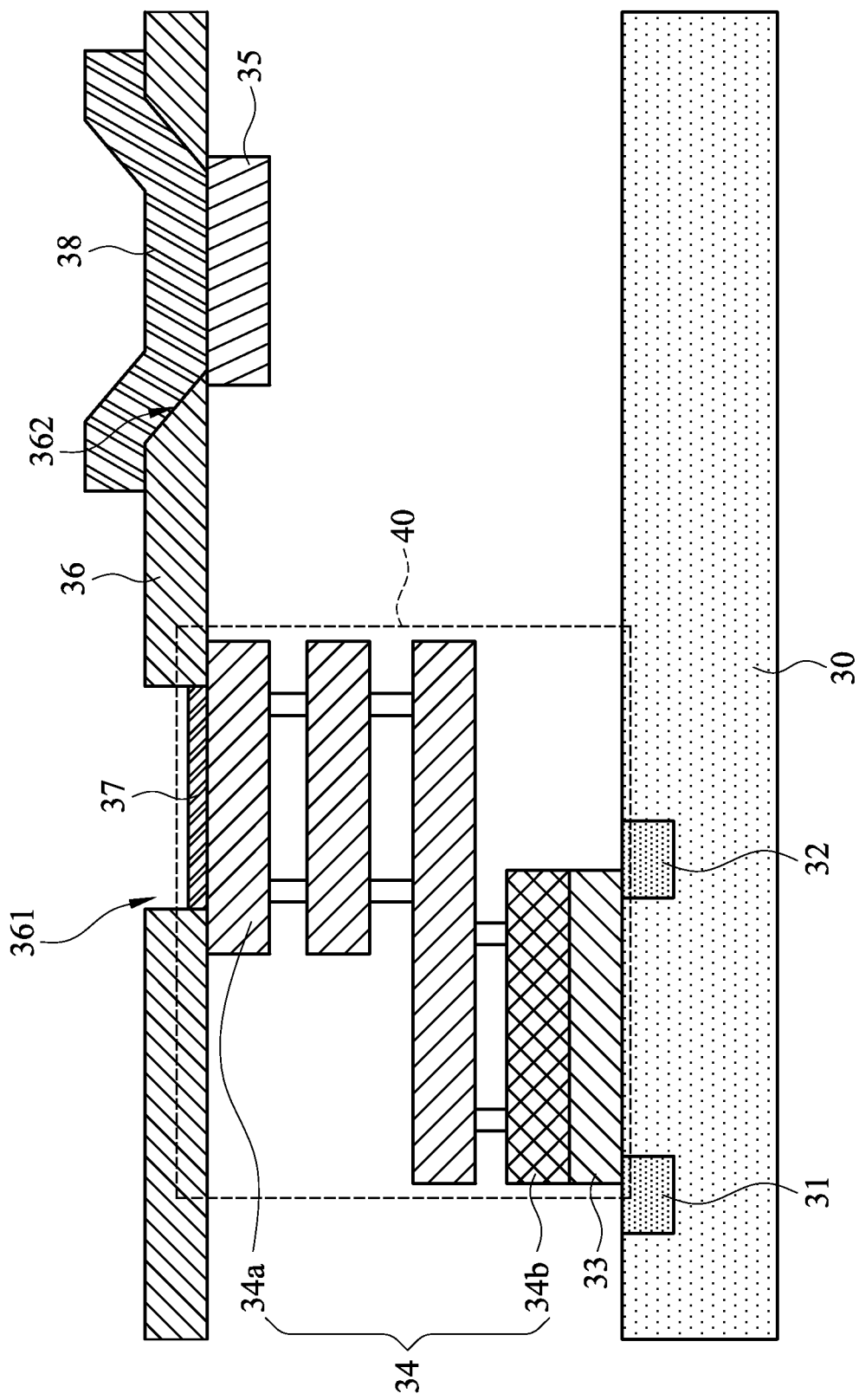

Please refer to FIG. 2B for a hydrogen ion-sensitive FET according to a second embodiment of the present invention. In the first embodiment described above, the first gate layer 34a within the gate area 40 makes direct contact with the insulating layer 33. In the second embodiment, however, besides the insulating layer 33 and the first gate layer 34a, there also exist additional metallic layers or gate layers within the gate area 40 for use as the transistor gate 34. As shown in FIG. 2B, the gate area 40 further includes a second gate layer 34b which is in direct contact with the insulating layer 33, and a sensing window is defined on the first gate layer 34a within the first opening 361, such that the first gate layer 34a automatically oxidizes to form the sensing film 37. Similarly, as shown in the right section of FIG. 2B, the conductor 35 may be formed at the same level as the first gate layer 34a so that the conductor 35 and the first gate layer 34a can be formed in the same manufacturing process.

It should be further noted that the sensing film 37 is not limited to being formed above the insulating layer 33 as shown in FIG. 2A. In other words, the position of the first opening 361 may be changed to define a sensing window elsewhere such that a different area of the first gate layer 34a automatically oxidizes to form the sensing film 37. Furthermore, as shown in FIG. 2B, the metallic or gate layers for use as the transistor gate 34 within the gate area 40 may vary in size and dimension and be arranged irregularly.

Figure 3:
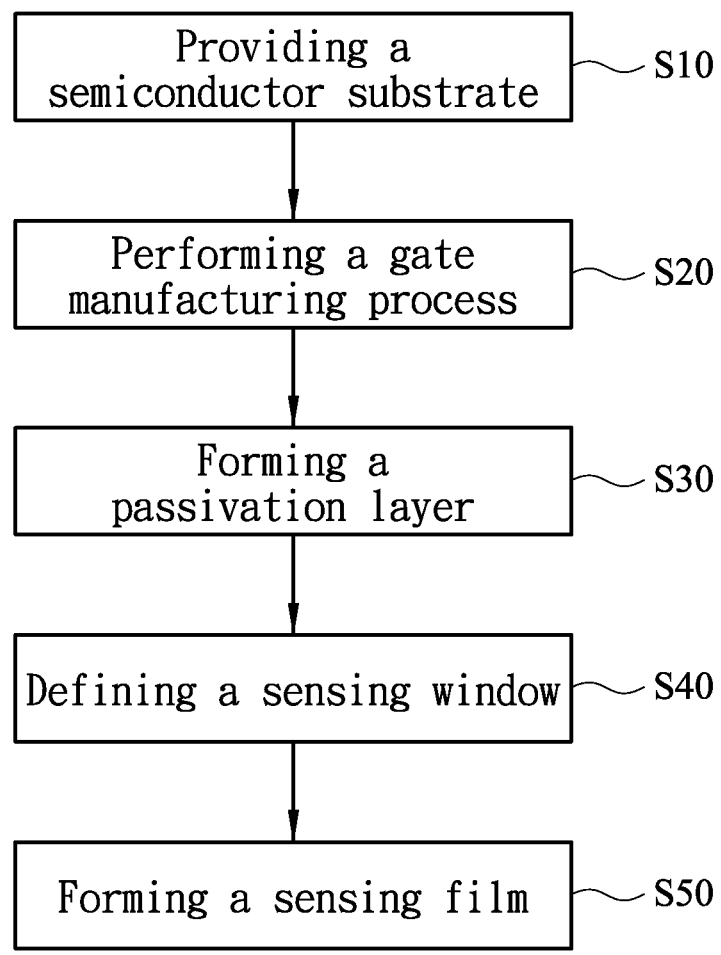
FIG. 3 is a flowchart of an embodiment of a method for manufacturing a hydrogen ion-sensitive FET according to the present invention.

FIG. 3 is a flowchart of an embodiment of a method for manufacturing a hydrogen ion-sensitive FET according to the present invention. For convenience, reference is also made to the structures shown in FIGS. 2A and 2B, and the reference numerals shown therein are also used. First, a semiconductor substrate 30 is provided (S10). The semiconductor substrate 30 already has a drain area 31, a source area 32, and an insulating layer 33 formed thereon, with the insulating layer 33 being located within a gate area 40 on the semiconductor substrate 30.

Next, a gate manufacturing process is performed (S20) to deposit an aluminum layer within the gate area 40, thus forming a first gate layer 34a in contact with the insulating layer 33 (as shown in FIG. 2A).

Additionally, in another embodiment, the gate manufacturing process (S20) includes forming a second gate layer 34b within the gate area 40, wherein the second gate layer 34b, rather than the first gate layer 34a, is in direct contact with the insulating layer 33 (as shown in FIG. 2B). Subsequent to the gate manufacturing process (S20), a passivation layer 36 is formed (S30). The passivation layer 36 is formed with a first opening 361 to expose a portion of the first gate layer 34a. Then, a sensing window is defined on the first gate layer 34a (S40). Finally, the sensing window of the first gate layer 34a is exposed to an oxygen-containing gas to form an alumina layer for use as a sensing film 37 (S50).

Furthermore, during the gate manufacturing process (S20), a conductor 35 may be simultaneously formed. Also, during formation of the passivation layer 36 (S30), a second opening 362 may be formed such that the conductor 35 is exposed through the passivation layer 36, and a reference electrode layer 38 can also be formed on the conductor 35, corresponding in position to the second opening 362 and be exposed through the passivation layer 36.

Figure 4:
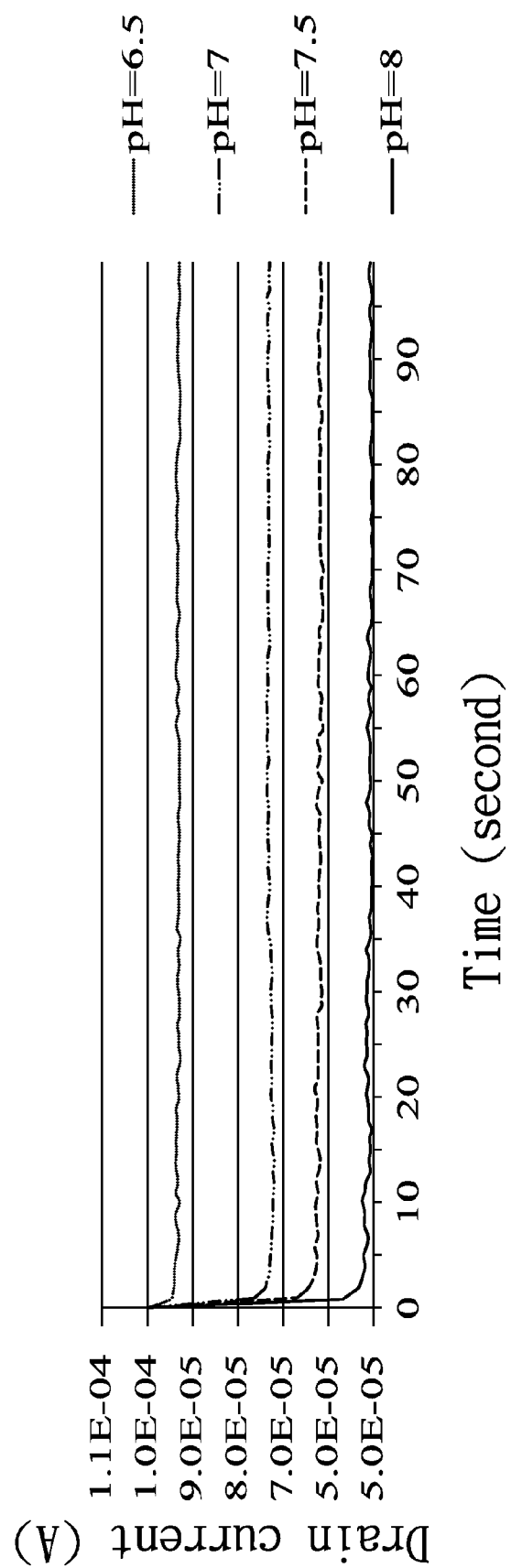
FIG. 4 illustrates measurement results obtained by using the hydrogen ion-sensitive FET of the present invention to measure the pH values of solutions.

In practical operation, when a bias voltage is applied to the reference electrode layer 38, hydrogen ions will be adsorbed to a surface of the sensing film 37 to cause a voltage variation at the transistor gate 34 and result in a different current. Therefore, the pH value of a solution can be sensed in this way. Reference measurement results of solutions with known pH values are shown in FIG. 4, wherein the pH values of the solutions range from 6.5 to 8, and the different pH values result in different currents when measured for different time durations, under the condition that Vg (gate voltage) and Vd (drain voltage) are fixed. Accordingly, in order to know the pH value of an unknown solution and thereby achieve the objective of measuring its hydrogen ions, a current from the unknown solution is measured and compared with the currents corresponding to the known pH value measurements so as to determine the pH value of the unknown solution.

The embodiments described above are only provided to demonstrate the features of the present invention so that those skilled in the art can understand the contents disclosed herein and implement the present invention accordingly. The embodiments are not intended to limit the scope of the present invention, which is defined only by the appended claims. Therefore, all equivalent modifications or alterations made without departing from the spirit of the present invention should fall within the scope of the claims.

What is claimed is:

1. A hydrogen ion-sensitive field effect transistor (FET), comprising:

a semiconductor substrate which has a gate area defined thereon and further has a source area and a drain area;

an insulating layer formed within the gate area on the semiconductor substrate;

a transistor gate deposited within the gate area and having a first gate layer, wherein the first gate layer is an aluminum layer and has a sensing window defined thereon; and a sensing film formed within the sensing window, wherein the sensing film is an alumina layer formed by oxidizing the first gate layer.

2. The hydrogen ion-sensitive FET of claim 1, wherein the first gate layer makes contact with the insulating layer.

3. The hydrogen ion-sensitive FET of claim 1, wherein the transistor gate further comprises a second gate layer, and the second gate layer makes contact with the insulating layer.

4. The hydrogen ion-sensitive FET of claim 1, further comprising a passivation layer formed with a first opening corresponding in position to the sensing window so as to expose the first gate layer.

5. The hydrogen ion-sensitive FET of claim 4, further comprising a conductor and a reference electrode layer, wherein the conductor and the transistor gate are formed in a same manufacturing process, and the reference electrode layer is provided on the conductor and exposed through the passivation layer.

* * * * *